United States Patent
Balthasar et al.

(10) Patent No.: US 9,557,265 B2
(45) Date of Patent: Jan. 31, 2017

(54) APPARATUS, SYSTEM AND METHOD FOR DETECTING MATTER

(71) Applicant: TOMRA SORTING AS, Asker (NO)

(72) Inventors: Dirk Balthasar, Boppard (DE); Ole Onsrud, Rasta (NO)

(73) Assignee: TOMRA SOTRING AS, Asker (NO)

( * ) Notice: Subject to any disclaimer, the term of this patent is extended or adjusted under 35 U.S.C. 154(b) by 68 days.

(21) Appl. No.: 14/373,928

(22) PCT Filed: Jan. 24, 2013

(86) PCT No.: PCT/NO2013/000001
§ 371 (c)(1),
(2) Date: Jul. 23, 2014

(87) PCT Pub. No.: WO2013/115650
PCT Pub. Date: Aug. 8, 2013

(65) Prior Publication Data
US 2014/0362382 A1 Dec. 11, 2014

(30) Foreign Application Priority Data
Jan. 24, 2012 (NO) .................................. 20120074

(51) Int. Cl.
*G01N 21/55* (2014.01)
*G01N 21/84* (2006.01)
*G02B 26/10* (2006.01)

(52) U.S. Cl.
CPC .............. *G01N 21/55* (2013.01); *G01N 21/84* (2013.01); *G02B 26/105* (2013.01); *G01N 2021/845* (2013.01); *G01N 2201/105* (2013.01)

(58) Field of Classification Search
CPC ..................................... G01N 21/55
USPC ......................................... 356/445
See application file for complete search history.

(56) References Cited

U.S. PATENT DOCUMENTS 3,176,306 A  3/1965 Burns
4,171,744 A * 10/1979 Hubbard .................. B07C 1/10
209/586

(Continued)

FOREIGN PATENT DOCUMENTS

CN    1495561 A    5/2004
CN    101690244 A   3/2010

(Continued)

OTHER PUBLICATIONS

An English Translation of Office Action (Notification of the First Office Action) issued on Sep. 16, 2015, by the Chinese Patent Office in corresponding Chinese Patent Application No. 2013800060716. (8 pages).

(Continued)

*Primary Examiner* — Roy M Punnoose
(74) *Attorney, Agent, or Firm* — Buchanan Ingersoll & Rooney P.C.

(57) ABSTRACT

An apparatus for detecting matter, the apparatus including: a first light source adapted to emit a first light beam; a second light source adapted to emit a second light beam, wherein the apparatus is arranged such that the first and second light beams converge towards a scanning element; the scanning element adapted to redirect the converging first and second light beams towards the matter to be detected; and a detector adapted to receive light reflected by the matter via the scanning element. Also, a system and method of detecting matter.

18 Claims, 5 Drawing Sheets

(56) References Cited

U.S. PATENT DOCUMENTS

| | | | | |
|---|---|---|---|---|
| 4,655,590 | A | * | 4/1987 | Aagano ............... G02B 27/108 219/121.76 |
| 4,723,659 | A | | 2/1988 | Billion |
| 5,122,659 | A | * | 6/1992 | Agano .................... H01S 3/094 219/121.61 |
| 5,134,278 | A | * | 7/1992 | Nelen .................. G01N 21/909 250/223 B |
| 6,449,036 | B1 | | 9/2002 | Wollmann et al. |
| 6,473,168 | B1 | * | 10/2002 | Ruymen ............ G01N 21/8901 356/237.2 |
| 6,614,531 | B2 | * | 9/2003 | Sato ......................... A24B 1/04 356/237.1 |
| 6,864,970 | B1 | * | 3/2005 | Ruymen ................. B07C 5/342 356/237.1 |
| 8,285,026 | B2 | * | 10/2012 | Dirix ..................... B07C 5/3422 382/141 |
| 9,147,253 | B2 | | 9/2015 | Yee et al. |
| 2002/0039185 | A1 | * | 4/2002 | Sato ......................... A24B 1/04 356/429 |
| 2010/0195058 | A1 | | 8/2010 | Ritz |

FOREIGN PATENT DOCUMENTS

| | | |
|---|---|---|
| CN | 102222329 A | 10/2011 |
| EP | 1 698 888 | 9/2006 |
| EP | 1 975 603 A1 | 10/2008 |
| JP | H-0862123 A | 3/1996 |
| JP | 2002-540397 A | 11/2002 |
| JP | 2005241336 A | 9/2005 |
| JP | 2009092481 A | 4/2009 |
| JP | 2011-506066 A | 3/2011 |
| WO | WO 98/44335 | 10/1998 |
| WO | 00/57160 A2 | 9/2000 |
| WO | 2009/076730 A2 | 6/2009 |

OTHER PUBLICATIONS

International Search Report (PCT/ISA/210) mailed on Apr. 24, 2013, by the European Patent Office as the International Searching Authority for International Application No. PCT/NO2013/000001.
Written Opinion of the International Searching Authority (PCT/ISA/220) by the European Patent Office as the International Searching Authority for International Application No. PCT/NO2013/000001.
Second Office Action dated Jun. 22, 2016 issued by the State Intellectual Property Office of the People's Republic of China in corresponding Chinese Patent Application No. 201380006071 6, and English language translation of Office Action (11 pages).
Office Action (Notice of Reasons for Rejection) issued on Oct. 18, 2016, by the Japanese Patent Office in Japanese Patent Application No. 2014-553271. (5 pages).

* cited by examiner

APPARATUS, SYSTEM AND METHOD FOR DETECTING MATTER

CROSS REFERENCE TO RELATED APPLICATIONS

The present application is a U.S. national stage application of International Application No. PCT/NO2012/000001, filed on Jan. 24, 2013, which claims the benefit of Norwegian Application No. 20120074, filed on Jan. 24, 2012. The entire contents of each of International Application No. PCT/NO2012/000001 and Norwegian Application No. 20120074 are hereby incorporated herein by reference in their entirety.

TECHNICAL FIELD

The disclosure relates to an apparatus for detecting matter. The disclosure also relates to a system and method of detecting matter.

BACKGROUND

U.S. Pat. No. 6,449,036 (Wollmann et al.) discloses a device wherein two lasers each generate a laser beam. The laser beams are deflected by mirrors and brought together into a common beam. For this purpose, one of the mirrors is transparent for the laser beam of the laser situated behind it. The combined laser beams pass through a hole in a further mirror and impinge on one of the plane polygon surfaces of a rotating polygonal mirror wheel. The polygonal mirror wheel guides the laser beams over a parabolic mirror, and the laser beam reflected by the parabolic mirror is guided to an inclined mirror and impinges on the surface of an object to be scanned. The object surface is projected onto the light receiver. A drawback with the device in U.S. Pat. No. 6,449,036 is that the laser is monochromatic.

WO9844335 A1 (Ruymen) discloses a device which can be mounted in a sorting apparatus. The device is provided with two light sources which each generate an intense, focused band of light. Both light sources generate light of different frequency and are brought together into a band of laser beams by a selectively semi-reflecting mirror (dichroic mirror) and an ordinary mirror. This light band is reflected towards a moving, prismatic mirror. The faces of this mirror are reflective and are set at essentially the same angle to one another. Furthermore, this prismatic mirror rotates around its central axis. The light band falling on such a face is directed towards the product to be sorted. As a result of the rotation of the mirror, the light band moves transversely across the stream of parts of the product. In doing so, said band moves each time in the same direction between two positions over the width of the stream of parts. When the light band falls on a part of the product, it is scattered and/or reflected by said part. Scattered light is at least partly captured by the same face, and, via said face, is led along approximately the same path as the light band to a beam splitter which reflects the scattered light at an angle towards two detectors. A drawback with the device in WO9844335 A1 is that the illumination is on the same optical path as the detection, whereby problems with total reflections may occur.

U.S. Pat. No. 3,176,306 relates to an apparatus for testing surface quality of material, and it discloses a "moving" slit viewing arrangement wherein a tin sheet which is again moves in a certain direction. Upper and lower light banks (line light sources) are mounted to give the desired off-specular angle of illumination and illuminate a strip of the tin sheet transverse to its direction of motion. A hood is positioned opposite the strip so as to restrict the view of a television camera to the strip.

SUMMARY

It is an object of embodiments of the disclosure to provide an improved apparatus and method for detecting matter.

According to an aspect of the disclosure, there is provided an apparatus for detecting matter, the apparatus comprising: a first light source adapted to emit a first light beam; a second light source adapted to emit a second light beam, wherein the apparatus is arranged such that the first and second light beams converge towards a scanning element; the scanning element adapted to redirect the converging first and second light beams towards the matter to be detected; and a detector adapted to receive light reflected by the matter via the scanning element.

The apparatus may further comprise a first mirror arranged in an optical path between the first light source and the scanning element, and a second mirror arranged in an optical path between the second light source and the scanning element, wherein the first mirror is adapted to redirect the first light beam and the second mirror is adapted to redirect the second light beam such that the first and second light beams converge towards a scanning element.

The distance between the first light source and the first mirror may be different than the distance between the second light source and the second mirror.

The detector may be arranged to receive reflected light travelling between the first and second light beams.

The detector may be positioned between the first and second mirrors, or a mirror element may be positioned between the first and second mirrors for redirecting reflected light to the detector.

A transportation means for transporting the matter may be provided below the apparatus.

The transportation means includes at least one of: a conveyor belt; a chute, and a free fall path.

The apparatus may further comprise a mounting plate, wherein at least the scanning element is mounted on the mounting plate, and wherein the mounting plate is arranged at an angle (A) of 2-15 deg., preferably about 10 deg., to the normal of the transportation means.

The apparatus according may be arranged such that the first and second light beams are substantially overlapping on the matter on the transportation means.

The apparatus may further comprise a first lens arranged between the first light source and the first mirror, and a second lens arranged between the second light source and the second mirror, wherein at least one of the first lens and the second lens is movable for adjusting the distance between the light source and the lens.

The apparatus may further comprise a housing accommodating at least the scanning element and having a bottom wall with a window below the scanning element, wherein at least one reference element is arranged next to said window.

Said reference element may comprises at least one of: a white reference including two (substantially) white reference areas and a central triangular mirror; a black or dark reference area; and an aperture in the bottom wall with a lens for collecting ambient light.

The scanning element may be one of a rotating polygon mirror and a tilting mirror. The first and second light sources may be point light sources, wherein the apparatus further comprises at least one line light source adapted to illuminate the matter.

The first and second light beams may be parallel or substantially parallel before being redirected by the first and second mirrors, wherein the first and second light sources and the first and second mirrors are arranged in a plane P perpendicular to a rotating or tilting plane of the scanning element, wherein one of the first and second mirrors is adapted to redirect the first light beam with less than 90 deg. in said plane P and the other of the first and second mirrors is adapted to redirect the second light beam with more than 90 deg. in said plane P, and wherein the detector or a mirror element adapted to redirect reflected light to the detector is positioned in said plane P between the first and second mirrors.

According to another aspect of the disclosure, there is provided a system comprising two apparatuses as defined above, arranged side by side such that the detection areas of the two apparatuses partly overlap.

The operation of the two apparatuses may be synchronized such that the overlap of the detection areas is not illuminated simultaneously by both apparatuses.

According to yet another aspect of the disclosure, there is provided a method of detecting matter, the method comprising: emitting a first light beam; emitting a second light beam; directing or redirecting the first light beam and the second light beam such that the first and second light beams converge towards a scanning element; redirecting the converging first and second light beams by means of the scanning element towards the matter to be detected; and receiving light reflected by the matter via the scanning element. This aspect may exhibit the same or similar features and technical effects as the previously described aspects, and vice versa.

BRIEF DESCRIPTION OF THE DRAWINGS

The disclosure will now be described in more detail, with reference to the appended drawings showing currently preferred embodiments of the disclosure.

DETAILED DESCRIPTION

Figure 1:
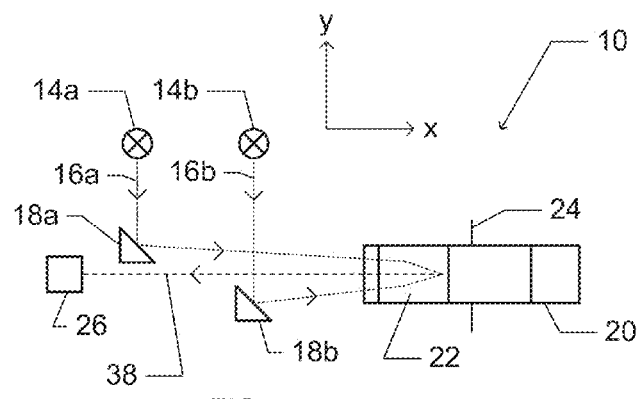
FIG. 1 is a schematic top view of an apparatus in accordance with an embodiment of the disclosure.
Figure 2:
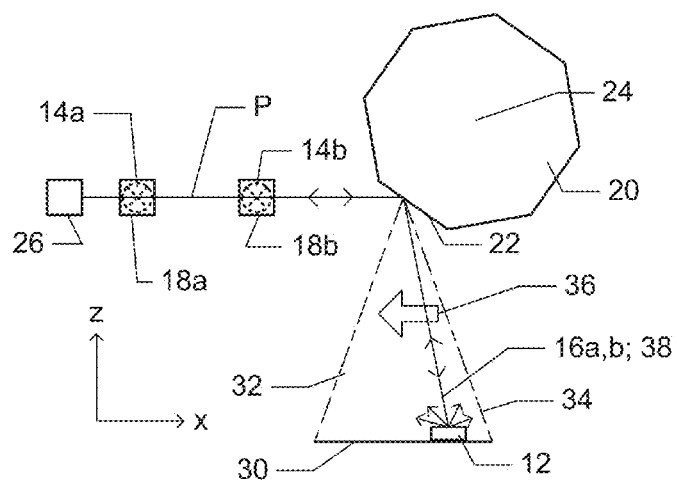
FIG. 2 is a side view of the apparatus of FIG. 1.
Figure 3:
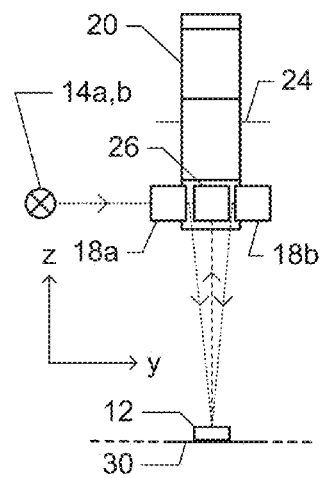
FIG. 3 is a front view of the apparatus of FIG. 1.

FIGS. 1-3 show an apparatus 10 for detecting matter 12.

The apparatus 10 comprises a first light source 14a and a second light source 14b. It should be noted that 'light' as used herein is not limited to electromagnetic radiation visible for the human eye, but may also include other wave lengths, in particular ultraviolet light and infrared light.

The first light source 14a is adapted to emit a first light beam 16a, whereas the second light source 14b is adapted to emit a second light beam 16b which is parallel to the first light beam, as seen e.g. in FIG. 1. The light sources 14a,b may be of the same type and emit the same kind of light. The light sources 14a,b may for instance be 55 W bulbs, but other light sources may be used as well. Further, the light sources 14a,b may be wide band sources, for example with emission of 400-1800 nm. Further, the light sources 14a,b may be point light sources, in contrast to the upper and lower light banks of U.S. Pat. no. 3,176,306.

The apparatus 10 further comprises a first mirror 18a and a second mirror 18b. The first and second mirrors 18a,b may be planar folding mirrors. The first mirror 18a is arranged at a distance in front of the first light source 14a and adapted to redirect the first light beam 16a. The second mirror 18b is arranged at greater a distance in front of the second light source 14b and adapted to redirect the second light beam. Specifically, the first mirror 18a is angled to redirect the first light beam 16a by just less than 90 deg., whereas the second mirror 18b is angled to redirect the second light beam 16b by just more than 90 deg., as seen in FIG. 1.

The apparatus 10 further comprises a scanning element or device, here a rotating polygon mirror 20. The polygon mirror 20 has a plurality reflecting faces 22. Further, the polygon mirror 20 is arranged to rotate around its central axis 24, for example by means of a motor (not shown). The polygon mirror 20 is adapted to further redirect the first and second light beams towards the matter 12.

The apparatus 10 further comprises a detector 26 adapted to receive light reflected by the matter 12 via the rotating polygon mirror 20. The detector 26 may for instance be a spectrometer. The detector 26 may be placed in the same plane P (defined by the x- and y-directions) as the first and second light source 14a,b and mirrors 18a,b, which plane P is perpendicular to the rotating plane of the polygon mirror 20, see for example FIGS. 2-3. Further, the detector 26 may be placed behind the mirrors 18a,b as seen in the x-direction, and between the mirrors 18a,b as seen in the y-direction.

In a method of detecting matter using the apparatus 10, the first and second parallel light beams 16a,b are generated using the first and second light sources 14a,b.

The first light beam 16a is redirected by the first mirror 18a, and the second light beam 16b is redirected by the second mirror 18b, whereby the redirected first and second light beam 16a,b converge towards the rotating polygon mirror 20. The converging light beams 16a,b falling on one of the faces 22 is further redirected towards and scanned over a transportation means, here a conveyor 30 on which the matter 12 to be detected is transported. It should be noted that when the beams 16a,b hit the face 22, they are not yet completely overlapping or converged, but they are closer to each other (in the y direction) than what they were at the mirrors 18a,b. Because of the rotation of the polygon mirror 20, the light beams 16a,b repeatedly moves transversely across the conveyor 30 in the same direction between two positions 32 and 34 over the width of the conveyor 30, as shown by the arrow 36 in FIG. 2. When the beams 16a,b via one of the faces 22 fall on the matter 12, the light of the beams 16a,b (which now are completely overlapping) is reflected by the matter 12. The reflection is typically diffuse, and the reflected light designated with reference sign 38 is at least partly captured by the same face 22, and led between the converging light beams 16a,b to the detector 26. Since the first and second mirrors 18a,b are sufficiently spaced apart in the y-direction, the reflected light 38 may pass between them and be received by the detector 26 (see FIG. 1).

Hence, in use any matter 12 on the conveyor 30 is illuminated by light from two light sources 14a,b. If one of the light sources 14a,b is broken, the apparatus 10 will still operate with only one light source. Also, since the light beams 16a,b are converging, total reflection(s) can be avoided.

Figure 4:
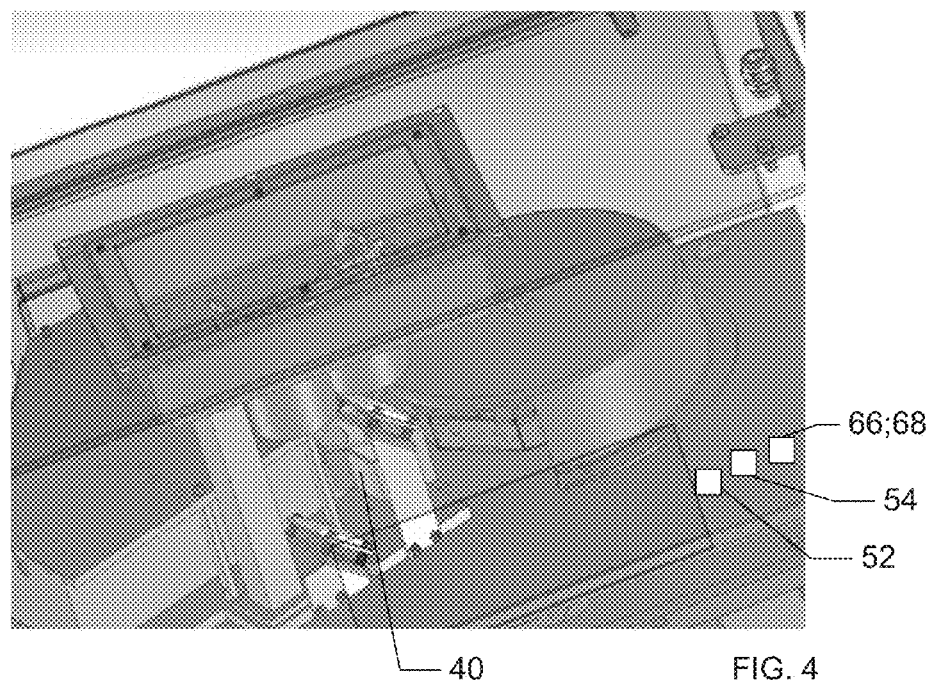
FIG. 4 is a partial perspective view of an apparatus in accordance with another embodiment of the disclosure.

The apparatus 10 in FIG. 4 is similar to that of FIGS. 1-3, but here the distance between the first light source 14a and mirror 18a is longer than the distance between the second light source 14b and mirror 18b. In this way, the first and second beams 16a,b do not intersect. Also, a mirror element 40 is positioned between the first and second mirrors 18a,b for redirecting reflected light to the detector 26. In this way, a bulky detector 26 will be out of the way of the light 16a,b,38.

Figure 5:
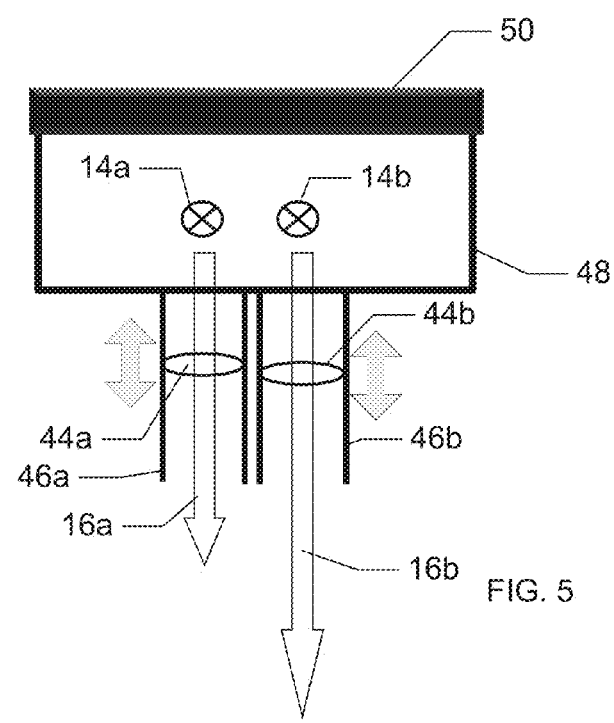
FIG. 5 is a schematic partial top view of the present apparatus.

The present apparatus 10 may further comprising a first lens 44a arranged between the first light source 14a and the first mirror 18a, and a second lens 44b arranged between the second light 14b source and the second mirror 18b, as seen in FIG. 5. The first and second lenses 44a,b are movable in the y-direction as indicated by the double arrows, whereby the distance between the respective light source 14a,b and lens 44a,b can be adjusted. In this way, the apparatus 10 may be setup and correctly focused depending on the distance to the conveyor 30. The first and second lenses 44a,b may for instance be focusing lenses. Preferably, each lens 44a,b is arranged in a respective tube 46a,b. Except for providing a path for the movement of the lenses 44a,b, the tubes 46a,b may also serve to collimate the light from the light sources 14a,b.

As further seen in FIG. 5 (and also in FIG. 4), the present apparatus 10 may further comprise a maintenance chamber 48 accommodating the first and second light sources 14a,b. The interior part of the maintenance chamber 48 is preferably insulated, and the door 50 is heat conductive and acts as a heat exchanger.

Figure 6:
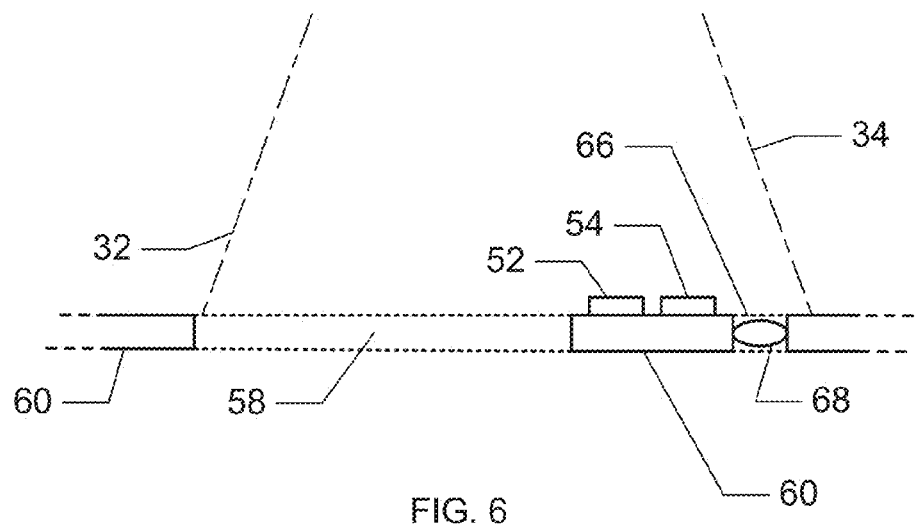
FIG. 6 is a schematic partial side view of the present apparatus.

The present apparatus 10 may further comprise at least one reference element, see FIGS. 4 and 6. The at least one reference element is placed next to or adjacent to a window 58 in the apparatus' housing 60 under the polygon mirror 20. To this end, the apparatus 10 is configured such that the first and second light beams 16a,b repeatedly are swept over the at least one reference element. Hence, as the polygon mirror 20 rotates, the detector 26 sees the at least one reference element with every scan line, and the apparatus 10 may be adjusted or calibrated accordingly. The at least one reference element may for instance be used to indicate light source aging and defect light sources. Also, by using a dark reference and a white reference (see below), no temperature calibration or compensation is necessary.

Figure 7:
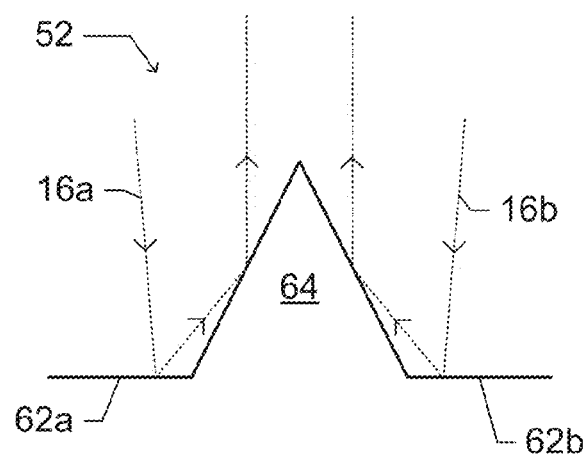
FIG. 7 is a front view of a white reference element in accordance with the p disclosure.

The at least one reference element may comprise a white reference element 52, as also shown in FIG. 7. The white reference 52 may include two white reference areas or surfaces 62a,b, and a triangular mirror 64 arranged between the two white areas 62a,b. The triangular mirror 64 may be equilateral or isosceles, wherein the two sides apart from the base are reflective. Upon operation, incoming light 16a,b is reflected by the white areas or surfaces 62a,b, and is redirected back towards the detector 26 by means of the triangular mirror 64.

Further, the at least one reference element may comprise a black or dark reference area 54. This area 54 may for instance be surface painted or coated black.

Further, the at least one reference element may comprise an aperture 66 in the bottom wall of the housing 60 with a lens 68 for collecting ambient light. In this way, the apparatus 10 may be adjusted or calibrated depending on how bright or dark the surrounding environment is, e.g. by subtracting the ambient light from the reflected light 38.

Figure 8:
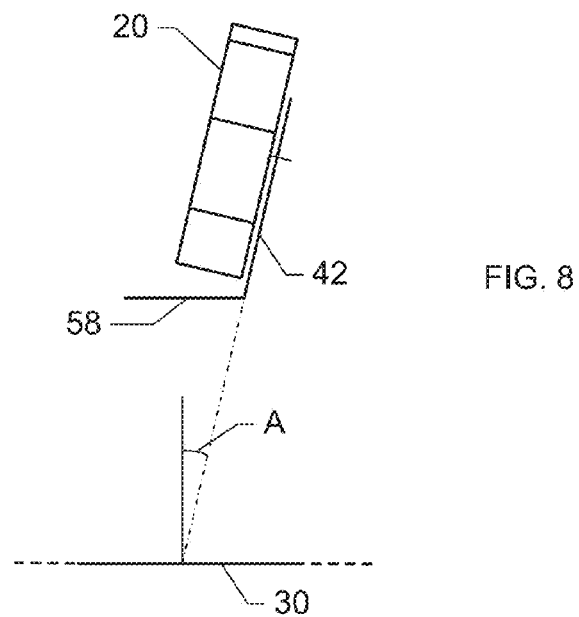
FIG. 8 is a schematic partial front view of the present apparatus.

The present apparatus 10 may further comprise a ground or mounting plate 42 as seen in FIG. 8. At least the polygon mirror 20 is mounted on the mounting plate 42, but preferably also the light sources 14a,b and mirrors 18a,b. The mounting plate 42 is arranged at an angle A of 2-15 deg., preferably about 10 deg., to the normal of the conveyor belt 30 and the front glass of window 58. In this way, total reflections (i.e. the angle of incidence is not zero) may be avoided, both from the matter 12/conveyor 30 and from the front glass of window 58.

Figure 9:
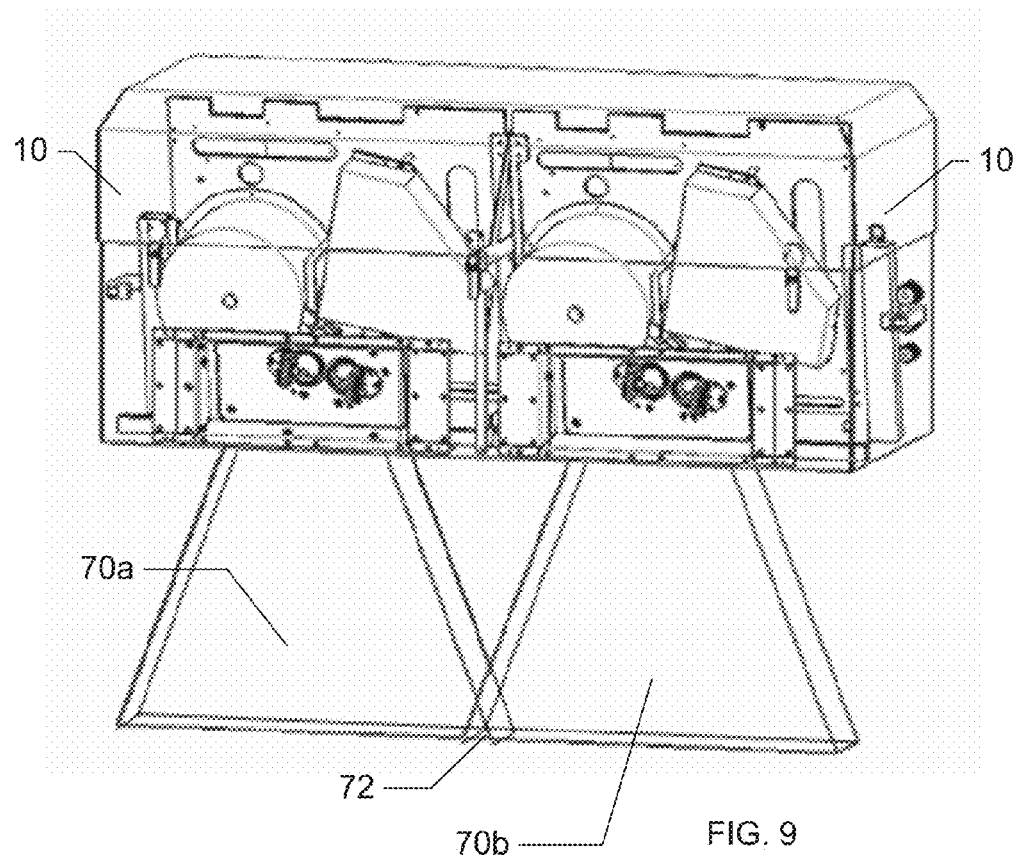
FIG. 9 illustrates a dual configuration of the disclosure.

Further, two apparatuses 10 may be arranged next to each other, with a somewhat overlapping detection areas 70a,b, as seen in FIG. 9. The overlap is designated with reference sign 72. By using two apparatuses 10 side by side, a wider conveyor 30 may efficiently be inspected. Further, the operation of the two apparatuses 10 may be synchronized such that the overlap 72 of the detection areas 70a,b is not illuminated simultaneously by both apparatuses 10. For this, a servo motor may be used to rotate the polygon mirrors.

Figure 10:
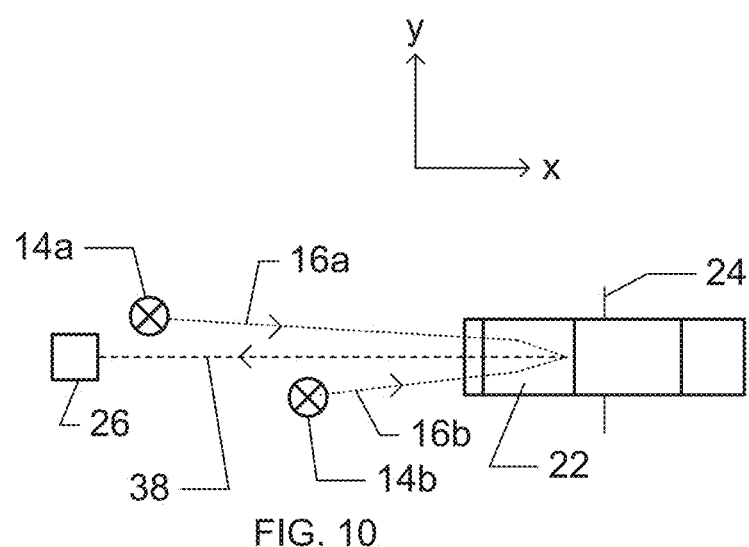
FIG. 10 is a schematic top view of an apparatus in accordance with yet another embodiment of the disclosure.

The apparatus 10 in FIG. 10 is similar to that of FIGS. 1-3, but here the first and second mirrors 18a,b are omitted. Instead, the first and second light sources 14a,b are directed such that the first and second light beams 16a,b converge towards the scanning element 20.

The present scanning apparatus 10 and method may be used to detect basically any matter 12 that gives a reflection within the electromagnetic field (electromagnetic signature). By using a spectrometer as detector 26, it is possible to detect not only that some matter 12 is present but also the type or material of the matter 12. Applications of the present apparatus 10 and method include but are not limited to various material sorting and recycling applications.

The person skilled in the art will realize that the disclosure by no means is limited to the embodiment(s) described above. On the contrary, many modifications and variations are possible within the scope of the appended claims.

For example, the conveyor 30 may be replaced by a chute or a free fall path.

Further, the polygon mirror may be replaced by a tilting mirror.

Further, the apparatus 10 may further comprises at least one line light source adapted to illuminate the matter. The at least one line light source may be adapted to illuminate the same area on the transportation means as the scanning beams from the first and second light sources. Further, the at least one line source may be adapted to emit light of a different wavelength or wavelength range compared to the first and second light sources, in order to broaden the range of the apparatus. Several sources may be combined: UV (ultraviolet), NIR (near infrared), MIR (middle infrared), and VIS (visible/visual) light.

The invention claimed is:

1. An apparatus for detecting matter, the apparatus comprising:
   a first light source configured to emit a first light beam;
   a second light source configured to emit a second light beam, wherein the apparatus is arranged such that the first and second light beams converge towards a scanning element;
   the scanning element configured to move in a rotating or tilting plane and to redirect the converging first and second light beams towards the matter to be detected, the apparatus being configured to emit the first and second light beams such that a plane P is defined by the first and second light beams, the plane P being perpendicular to the rotating or tilting plane of the scanning element; and a detector configured to receive light reflected by the matter via the scanning element.

2. The apparatus according to claim 1, further comprising a first mirror arranged in an optical path between the first light source and the scanning element, and a second mirror arranged in an optical path between the second light source and the scanning element, wherein the first mirror is configured to redirect the first light beam and the second mirror is configured to redirect the second light beam such that the first and second light beams converge towards the scanning element.

3. The apparatus according to claim 2, wherein the distance between the first light source and the first mirror is different than the distance between the second light source and the second mirror.

4. The apparatus according to claim 1, wherein the detector is arranged to receive reflected light travelling between the first and second light beams.

5. The apparatus according to claim 2, wherein the detector is positioned between the first and second mirrors, or wherein a mirror element is positioned between the first and second mirrors for redirecting reflected light to the detector.

6. The apparatus according to claim 1, wherein a transportation means for transporting the matter is provided below the apparatus.

7. The apparatus according to claim 6, wherein the transportation means includes at least one of: a conveyor belt; a chute; and a free fall path.

8. The apparatus according to claim 6, further comprising a mounting plate, wherein at least the scanning element is mounted on the mounting plate, and wherein the mounting plate is arranged at an angle of 2-15 deg. to the normal of the transportation means.

9. The apparatus according to claim 6, arranged such that the first and second light beams are substantially overlapping on the matter on the transportation means.

10. The apparatus according to 2, further comprising a first lens arranged between the first light source and the first mirror, and a second lens arranged between the second light source and the second mirror, wherein at least one of the first lens and the second lens is movable for adjusting the distance between the light source and the lens.

11. The apparatus according to claim 1, further comprising a housing accommodating at least the scanning element and having a bottom wall with a window below the scanning element, wherein at least one reference element is arranged next to said window.

12. The apparatus according to claim 11, wherein said reference element comprises at least one of:

a white reference including two substantially white reference areas and a central triangular mirror;
a black or dark reference area; and
an aperture in the bottom wall with a lens for collecting ambient light.

13. The apparatus according to claim 1, wherein the scanning element is one of a rotating polygon mirror and a tilting mirror.

14. The apparatus according to claim 1, wherein the first and second light sources are point light sources.

15. The apparatus according to claim 2, wherein the first and second light beams are parallel or substantially parallel before being redirected by the first and second mirrors, wherein the first and second light sources and the first and second mirrors are arranged in the plane P perpendicular to the rotating or tilting plane of the scanning element, wherein one of the first and second mirrors is configured to redirect the first light beam with less than 90 deg. in said plane P and the other of the first and second mirrors is configured to redirect the second light beam with more than 90 deg. in said plane P, and wherein the detector or a mirror element configured to redirect reflected light to the detector is positioned in said plane P between the first and second mirrors.

16. A system comprising two apparatuses according to claim 1 arranged side by side such that the detection areas of the two apparatuses partly overlap.

17. A system according to claim 16, wherein the operation of the two apparatuses is synchronized such that the overlap of the detection areas is not illuminated simultaneously by both apparatuses.

18. A method of detecting matter, the method comprising:
emitting a first light beam;
emitting a second light beam;
directing or redirecting the first light beam and the second light beam such that the first and second light beams converge towards a scanning element, the scanning element being configured to move in a rotating or tilting plane;
causing the first and second light beams to be emitted such that a plane P is defined by the first and second light beams, the plane P being perpendicular to the rotating or tilting plane of the scanning element;
redirecting the converging first and second light beams by means of the scanning element towards the matter to be detected; and
receiving light reflected by the matter via the scanning element.

* * * * *